United States Patent [19]

Baggiolini et al.

[11] 4,245,104

[45] Jan. 13, 1981

[54] ISOXAZOLINES AND ISOXAZOLIDINES

[75] Inventors: Enrico G. Baggiolini, Nutley; Hsi L. Lee, West Paterson; Milan R. Uskokovic, Upper Montclair, all of N.J.

[73] Assignee: Hoffmann-La Roche Inc., Nutley, N.J.

[21] Appl. No.: 965,660

[22] Filed: Dec. 1, 1978

Related U.S. Application Data

[63] Continuation-in-part of Ser. No. 822,119, Aug. 5, 1977, Pat. No. 4,130,713.

[51] Int. Cl.$^3$ .......................................... C07P 515/04
[52] U.S. Cl. ........................... 548/207; 549/71; 548/324
[58] Field of Search .................. 260/307 F, 307 FA; 548/207

[56] References Cited

U.S. PATENT DOCUMENTS

| 2,489,235 | 11/1949 | Goldberg et al. | 548/303 |
| 2,489,236 | 11/1949 | Goldberg et al. | 548/303 |
| 2,489,237 | 11/1949 | Goldberg et al. | 548/303 |
| 3,740,416 | 6/1973 | Gerecke et al. | 548/303 |
| 3,957,794 | 5/1976 | Baggiolini et al. | 546/114 |

OTHER PUBLICATIONS

Baker et al., "J. Org. Chem.," vol. 12, pp. 167-173.
Harris et al., "Science," 97, pp. 447 & 448, (1943).
Wolf et al., J.A.C.S., 67, pp. 2100-2102, (1945).

*Primary Examiner*—Donald G. Daus
*Assistant Examiner*—D. B. Springer
*Attorney, Agent, or Firm*—Jon S. Saxe; Bernard S. Leon; George W. Johnston

[57] ABSTRACT

A process is disclosed for producing d-biotin from L-cystine via novel intermediates.

8 Claims, No Drawings

ISOXAZOLINES AND ISOXAZOLIDINES

RELATED APPLICATIONS

This application is a continuation-in-part application of U.S. Patent Application Ser. No. 822,119, filed Aug. 5, 1977, now U.S. Pat. No. 4,130,713.

BACKGROUND OF THE INVENTION

This invention relates to a process for preparing d-biotin.

Optically active d-biotin, also known as Vitamin H, is a natural product found in kidneys, livers, egg yolks, milk and yeast. The compound can be utilized to prevent the symptoms of egg white injury in experimental animals and is used medicinally to treat various dermatitides.

Biotin has been prepared synthetically by Harris et al. (Science, Vol. 97, pg. 447, 1943) and Baker et al. (J. Org. Chem., Vol. 12, p. 167, 1947) and the first commercial synthesis resulted from the work of Goldberg and Sternbach as described in U.S. Pat. Nos. 2,489,235 and 2,489,236. The prior art processes for the production of optically active d-biotin proceeded via racemic intermediates and thus formed racemic mixtures of biotin. To produce the desired d-enantiomer, the resulting biotin had to be resolved by costly and time consuming techniques which led to a decrease in yield of the desired product.

SUMMARY OF THE INVENTION

We have invented a novel process for the synthesis of optically active d-biotin of the formula:

[Structure I: bicyclic biotin structure with HN-C(=O)-NH, S, and (CH$_2$)$_4$COOH side chain]

from optically active L-(-)-cystine of the formula:

[Structure II: (H$_2$N-CH(COOH)-CH$_2$-S-)$_2$]

via optically active intermediates.

In accordance with the present invention, L-(-)-cystine is transformed through various optically active intermediates to a transient nitrile oxide of the formula:

[Structure X: HN(COOR$_1$)-CH-CH$_2$-S-CH=C((CH$_2$)$_3$R$_2$)-C≡N$^+$-O$^-$]

wherein
R$_1$ is alkyl or aryl;
R$_2$ is methyl or —CH$_2$OR$_3$; and,
R$_3$ is lower alkyl, aryl or aryl (lower) alkyl. The nitrile oxide is then cyclized by an intramolecular 1,3 dipolar addition to its double bond to form an isomeric mixture which includes optically active isoxazolines of the formulas:

[Structure XI: isoxazoline with COOR$_1$, HN, N-O ring, S, H, (CH$_2$)$_3$R$_2$]

and

[Structure XII: isoxazoline isomer with COOR$_1$, HN, N-O ring, S, H, (CH$_2$)$_3$R$_2$]

wherein R$_1$ is lower alkyl or aryl; R$_2$ is methyl or —CH$_2$OR$_3$; and R$_3$ is lower alkyl, aryl or aryl (lower) alkyl.

The noted isoxazolines (individually or as a mixture) are transformed through various novel optically active intermediates to a known optically active compound of the formula:

[Structure XIX: bicyclic structure with HN-C(=O)-NH, S, and (CH$_2$)$_4$R$_2$ side chain]

wherein
R$_2$ is methyl or —CH$_2$OR$_3$; and
R$_3$ is lower alkyl, aryl or aryl (lower) alkyl.

Compound XIX is converted to d-biotin of formula I by known techniques.

The process of the present invention advantageously is carried out without racemization ultimately to form optically active d-biotin thus obviating the need for resolution.

DETAILED DESCRIPTION

The present invention concerns a novel process for the production of optically active d-biotin from optically active L-cystine via optically active intermediates.

As used herein, alkyl connotes straight or branched chain saturated aliphatic hydrocarbon groups containing 1 to 20 carbon atoms. Lower alkyl means alkyl groups having from 1 to 7 carbon atoms, (e.g., methyl, ethyl, n-propyl and isopropyl). Lower alkoxy means alkoxy groups having from 1 to 7 carbon atoms (e.g. methoxy, ethoxy and isopropoxy). Lower alkylene denotes alkylene groups of 2-6 carbon atoms (e.g., ethylene, propylene and butylene). Lower alkanol connotes alkanols having 1-7 carbon atoms (e.g., methanol and propanol). Lower alkylenedioxy denotes a moiety derived by the condensation of the hydroxy group of a 1,2 or 1,3 diol with a carbonyl function. The alkylene group of lower alkylenedioxy has 2 to 5 carbon atoms. Typical lower alkylenedioxy groups are ethylenedioxy, 1,2 propylenedioxy, 2,4 butylenedioxy and 2,3 pentylenedioxy.

Aryl denotes mononuclear aromatic hydrocarbon groups such as phenyl and the like which can be unsubstituted or substituted in one or more positions with halogen, nitrogen, lower alkylenedioxy, lower alkyl or lower alkoxy as well as polynuclear aryl groups such as napthyl, anthryl, phenanthryl, azulyl and the like which can be unsubstituted or substituted with one or more of the aforementioned substituents.

Arylalkyl connotes a group comprising alkyl and aryl moieties as defined hereinbefore. Aryl (lower) alkyl defines a group comprising lower alkyl and aryl moieties as defined hereinbefore, particularly benzyl and α-lower alkyl substituted benzyls (e.g., cumyl). Halogen denotes chlorine, bromine and iodine. Alkali metals include lithium, sodium, potassium and rubidium. Alkaline earth metals include beryllium, magnesium, calcium and strontium.

In the pictorial representations of the compounds of this application, a solid tapering line ( ■— ) indicates a substituent which is in the β-orientation (above the plane of the molecule) and a dashed line (---) indicates a substituent which is in the α-orientation (below the plane of the molecule). A wavy line ( ∼∼∼ ) indicates a Z and E mixture of the represented compound.

In accordance with the present invention, d-biotin of the formula:

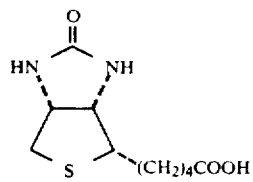

is produced from L-cystine of the formula:

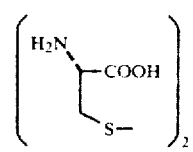

by the following reaction scheme:

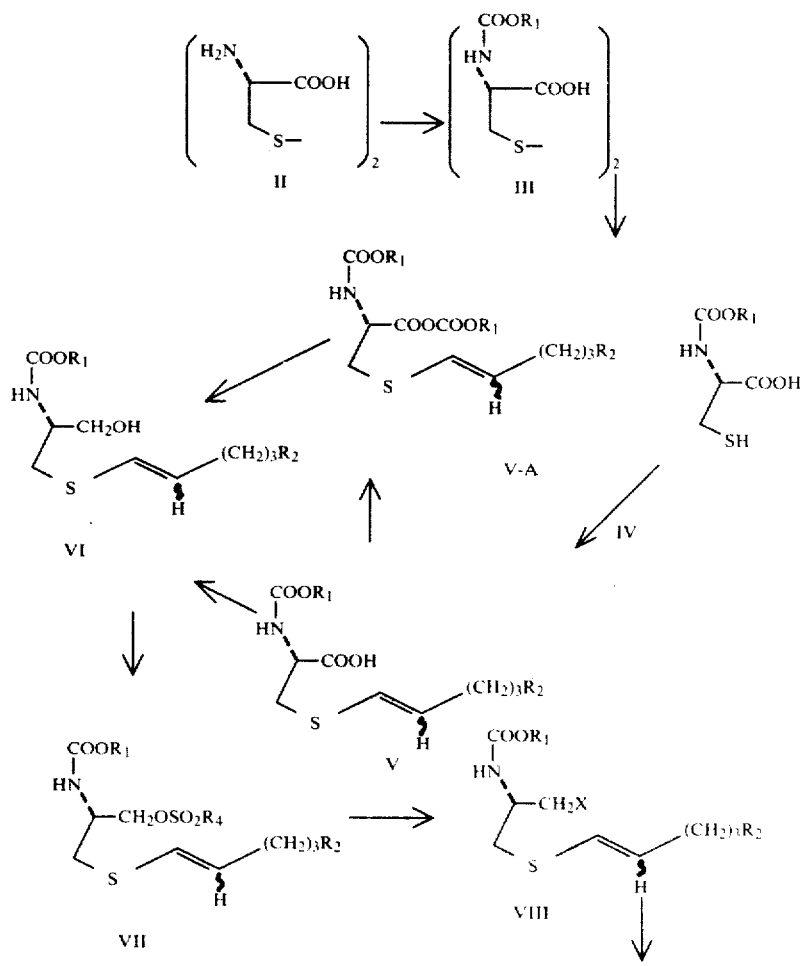

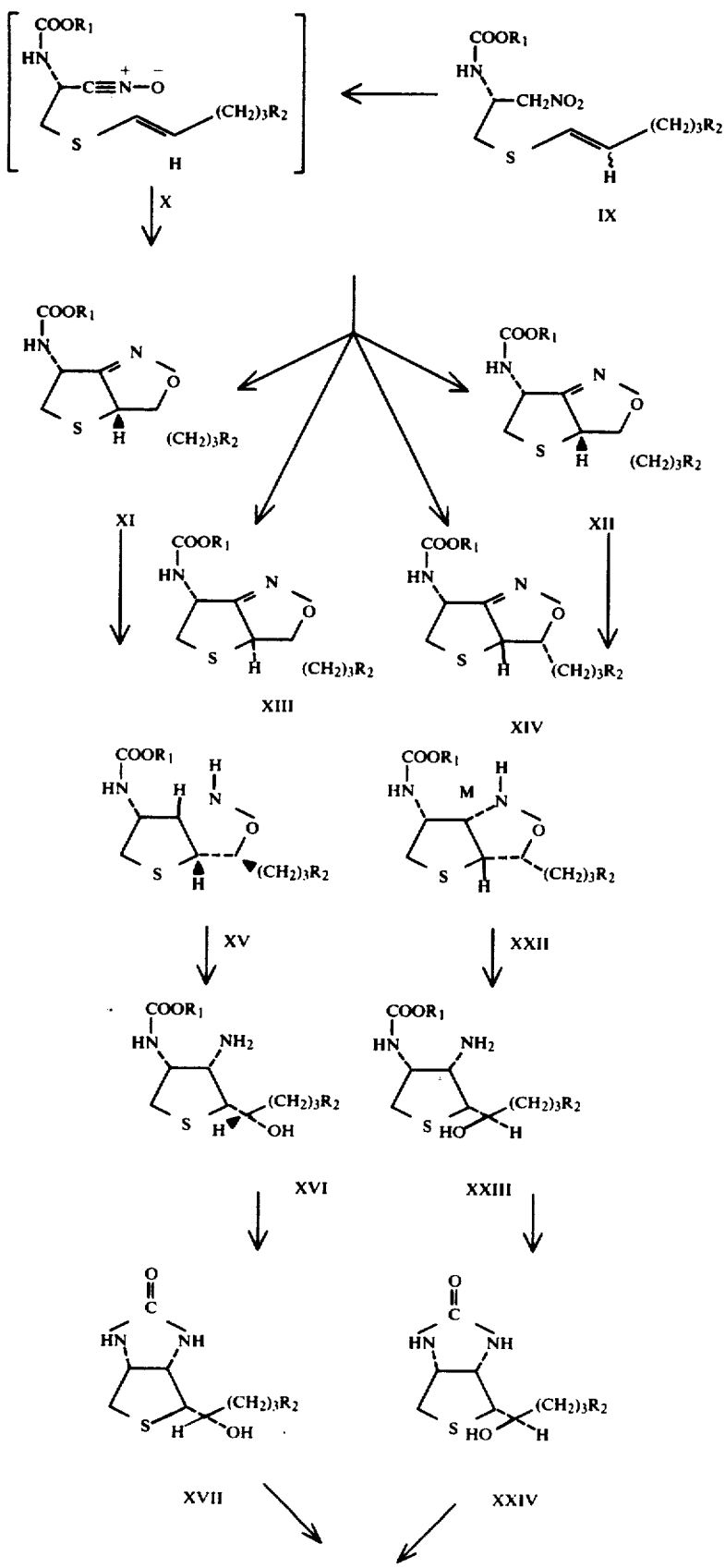

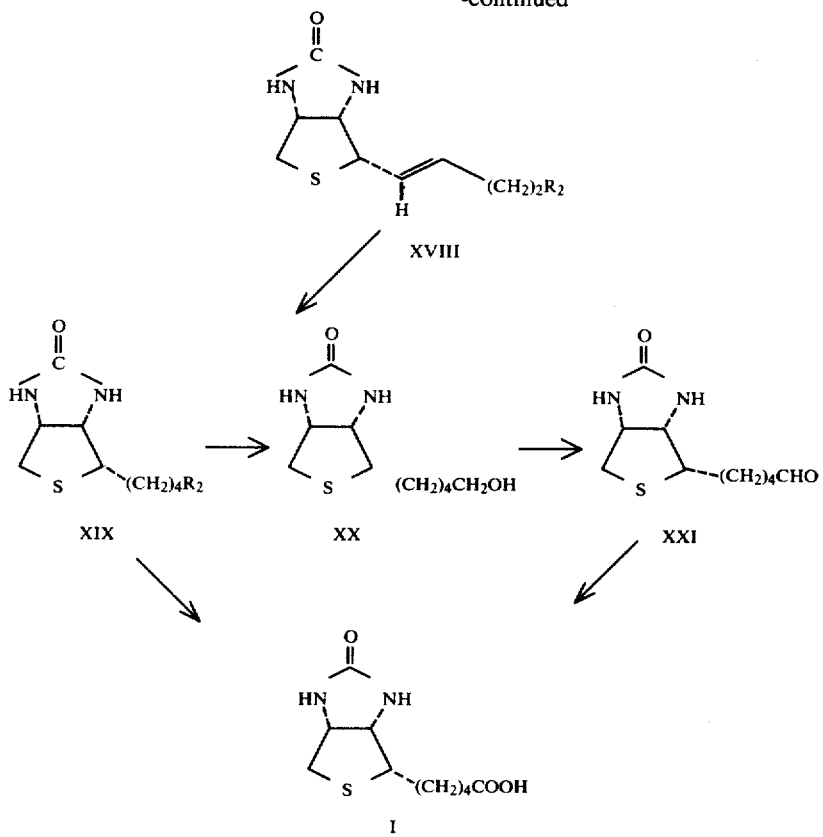

wherein

R₁ and R₄ each are lower alkyl or aryl;

R₂ is methyl or —CH₂OR₃;

R₃ is lower alkyl, aryl or aryl (lower) alkyl; and X is halide.

In accordance with the above noted scheme, L-cystine of formula II is acylated at the nitrogen atom to form a urethane of formula III according to conventional techniques. More particularly, L-cystine of formula II is reacted with a lower alkyl haloformate or aryl haloformate (e.g., methylchloroformate, ethylchloroformate and phenylbromoformate) in basic media to form compound III. The base media may be inorganic or organic. Typical inorganic bases include alkali metal hydroxides, carbonates and bicarbonates (e.g., sodium hydroxide, sodium carbonate and potassium bicarbonate) and the organic bases include tertiary amines (e.g. pyridine and triethyl amine). Although not necessary, the reaction may proceed in an inert organic solvent (e.g., dioxane and tetrahydrofuran) or an aqueous mixture thereof (e.g. mixture of water and tetrahydrofuran). The temperature is not critical but the reaction is generally carried out between about −30° and about 30° C., preferably at 0° C.

The urethane of formula III is reduced to the mercaptan of formula IV via any conventional means for selectively reducing a disulfide bond. A suitable technique includes reacting compound III with a hydride reducing agent such as an alkali metal or alkaline earth metal borohydride (e.g., sodium borohydride and magnesium borohydride) in an appropriate organic solvent (e.g. methanol, ethanol and hexanol for sodium borohydride and diethyl ether for magnesium borohydride). Although the temperature is not critical, the reaction generally proceeds from about −10° to about 30° C., preferably at 0° C.

In another method for converting compound III to compound IV, compound III is reacted with a dissolved alkali metal reducing agent such as sodium in liquid ammonia at a temperature of about −80° to about 0° C. and preferably at about −40° C.

Compound IV is reacted with 1-hexyne or 6-lower alkoxy, 6-aryl (lower) alkoxy or 6-aryloxy substituted 1-hexynes in the presence of a radical initiator to form an olefinic carboxylic acid mixture of Z and E geometric isomers of formula V. Typical substituted acetylenic compounds include 6-ethoxy-1-hexyne, 6-benzyloxy-1-hexyne and 6-phenoxylhexyne. Any conventional radical initiator such as benzoyl peroxide, 2′,2′-bisazo-(2-methylpropionitrile), di-t-butyl peroxide or dicumene may be utilized in in this reaction. The conversion of compound IV to compound V is carried out in an inert organic solvent such as an ether (e.g., diethyl ether, dioxane and tetrahydrofuran) or an aromatic hydrocarbon (e.g., benzene and toluene). The reaction is carried out at a temperature sufficient to decompose the radical initiator and generally ranges from about 50° to about 150° C. depending upon the initiator utilized.

The carboxylic acid of formula V is reduced to an alcohol mixture of Z and E geometric isomers of formula VI by any conventional means for selectively reducing a carboxylic acid to an alcohol without affecting an urethane moiety. An acceptable reducing agent for this selective reduction is diborane in an inert organic solvent such as an aliphatic (e.g., pentane and hexane), or aromatic (e.g. benzene and toluene), hydrocarbon or an ether (e.g. diethyl ether and dioxane). The reaction temperature generally ranges from about −30° to about 30° C. Preferably the reaction proceeds at about 0° C.

Compound V also can be converted to compound VI via intermediate V-A. Compound V first is reacted with a lower alkyl haloformate or aryl haloformate to form anhydride V-A which is then converted via a hydride reducing agent to compound VI. Typical lower alkyl haloformates or aryl haloformates include methyl chloroformate, ethyl chloroformate and phenyl bromoformate. Suitable hydride reducing agents include complex borohydrides of alkali metals and alkaline earth metals (e.g., sodium borohydride and potassium borohydride and magnesium borohydride). The formation of the anhydride V-A and the reduction thereof occurs in an inert organic solvent (e.g., hexane, benzene and diethyl ether) and at a temperature of about −20° to about 30° C., preferably at about 0° C.

The alcohol of formula VI is then reacted with a lower alkyl halosulfonate or aryl halosulfonates (e.g., methyl sulfonyl chloride and paratoluene sulfonyl bromide) in the presence of a tertiary amine such as pyridine and triethyl amine to form a sulfonate mixture of Z and E geometric isomers of formula VII. Although not necessary, the reaction is preferably carried out in an inert organic solvent such as an ether (e.g., diethyl ether and tetrahydrofuran) or an aromatic hydrocarbon (e.g. benzene and toluene). Although temperature is not critical, the reaction proceeds generally between about −20° and about 60° C. A temperature of about 0° C. is preferred.

Compound VII is treated with an alkali metal halide in a suitable solvent to form a halide mixture of Z and E geometric isomers of formula VIII. Among the preferred alkali metal halogenates are sodium iodide, sodium bromide and potassium bromide. Typical solvents include dialkyl ketones such as acetone, dialkyl sulfoxides such as dimethyl sulfoxide and dialkyl amides such as dimethylformamide. The reaction is generally carried out between about room temperature to about 100° C. and preferably at about 50° to 70° C.

The compound of formula VIII is converted to a nitro olefin mixture of Z and E geometric isomers of formula IX by reacting compound VIII with an alkali metal nitrite. Among the preferred alkali metal nitrites are sodium nitrite, potassium nitrite and lithium nitrite. The reaction proceeds in an organic solvent having a high dielectric constant. Suitable solvents include dimethyl formamide, hexamethyl phoshoramide and dimethyl sulfoxide. The formation of compound IX from compound VIII generally occurs at a temperature between about 10° and about 50° C. and preferably at about room temperature.

The nitro-olefins of formula IX are dehydrated to the isomeric isoxazolines of formulas XI through XIV via a transient intermediate of formula X. The conversion of the nitro-olefin IX to the isooxazolines of formula XI through XIV proceeds by an intramolecular 1,3 dipolar addition of the transient intermediate X to its double bond and results in the formation of a 5,5-bicyclic ring system. This conversion is carried out by treating compound IX with a dehydrating agent. Suitable dehydrating agents include alkyl or aryl isocyanates such as methyl isocyanate, isopropyl isocyanate and phenyl isocyanate. The reaction proceeds in an inert organic solvent such as an aliphatic (e.g., pentane and hexane) or aromatic (e.g. benzene and toluene) hydrocarbon and an ether (dioxane and tetrahydrofuran). Although not critical, the temperature generally ranges from about 10° to about 80° C. The reaction preferably proceeds at about room temperature.

The isomeric isoxazolines of formulas XI through XIV can be separated from each other by conventional separation techniques. For example, compounds XI and XII can be separated from compounds XIII and XIV by open column chromatograph on silica. Compounds XI and XII can then be separated from each other preferably by high pressure liquid chromatography on silica.

According to one aspect of the present invention, compound XI can be utilized to form d-biotin of formula I. More particularly, the isoxazoline XI is first reduced to isoxazolidine of formula XV by any hydride reducing agent which is capable of selectively reducing an isoxazoline without attacking a urethane group. Suitable reducing agents include diborane and a dialkyl aluminum hydride (e.g., diisobutyl aluminum hydride). This reduction is carried out in an inert solvent such as an aliphatic (e.g., isopropane) or aromatic (e.g., benzene) hydrocarbon or an ether (e.g., diethylether). When utilizing diborane, the conversion of compound XI to compound XV generally proceeds between about −30° and about 30° C. and preferably at about 0° C. When utilizing a dialkyl aluminum hydride, the reaction generally proceeds at about −80° C. to about −20° C. and preferably at about −60° C. to about −50° C.

Isoxazolidine XV is then converted to an amino alcohol of formula XVI by catalytic hydrogenation in a suitable solvent. Typical catalysts include platinum, palladium on charcoal and Raney nickel. Any organic solvent utilized in conventional catalytic hydrogenation may be employed. Suitable solvents include organic alcohols such as methanol, isopropanol and hexanol as well as acetic acid. Although not critical, the temperature of the noted reaction generally ranges from about 0° to about 50° C. Room temperature is preferred.

Amino alcohol XVI can then be cyclized to an imidazolone of formula XVII by treatment with a base. Suitable bases include alkali metal and alkaline earth metal hydroxides and alkoxides (e.g. sodium hydroxide, barium hydroxide and potassium alkoxide) as well as tertiary amines (pyridine and triethyl amine). Although not necessary, any conventional organic solvent or aqueous mixture thereof may be employed in the reaction. Typical solvents include dioxane and diethyl ether. In the conversion of compound XVI to compound XVII, temperature can range from about 50° to about 150° C. When barium hydroxide is utilized with a dioxane-water mixture, reflux temperature is preferred.

Imidazolone XVII can be converted to an olefinic mixture of Z and E geometric isomers of the formula XVIII by dehydration. For example, compound XVII can be reacted in the presence of paratoluene sulfonic acid in an inert aromatic solvent such as toluene to produce the geometric isomers of formula XVIII. The temperature of the reaction generally ranges from about 60° C. to about 130° C. When toluene is the solvent, a temperature of about 100° C. is preferred.

Compound XVIII can be converted to the known compound XIX via catalytic hydrogenation. Any conventional catalytic hydrogenation technique may be employed. Typical catalyst include palladium on charcoal, palladium on barium sulfate, platinum and Raney nickel. Any conventional solvent utilized in catalytic hydrogenation may be employed. Suitable solvents include organic alcohols (e.g. methanol, propanol and hexanol), acetic acid and water mixtures thereof. Although not critical, the temperature and pressure can range from about 5° to about 200° C. and from atmospheric pressure to about 500 psi. When palladium on charcoal is selected as the catalyst, room temperature and atmospheric pressure are preferred.

The conversion of compound XIX to d-biotin may be effectuated in various ways depending on the $R_2$ substituent. When $R_2$ is methyl, compound XIX is directly converted to d-biotin by microbiological oxidation techniques. The microbiological oxidation technique disclosed in U.S. Pat. No. 3,359,167 issued to Ogino et al. is preferably employed. According to the Ogino et al. procedure, compound XIX wherein $R_2$ is methyl is converted to d-biotin by treatment with the organism *Corynebacterium Primorioxydans.*

When $R_2$ is —$CH_2OR_3$ and $R_3$ is lower alkyl, aryl or aryl(lower)alkyl, compound XIX is converted to d-biotin of formula I via intermediates of formulas XX and XXI.

When $R_3$ is lower alkyl, aryl or aryl(lower)alkyl, compound XIX is converted to alcohol XX by conventional procedures for removing ether protecting groups. A suitable technique includes acid-catalyzed hydrolysis of compound XIX. Conventional strong aqueous inorganic acid may be utilized. Typical acids include aqueous hydroiodic, hydrobromic and hydrochloric acid. The reaction generally proceeds at reflux temperature.

Alternatively, when $R_3$ is benzyl or α-substituted benzyl, the conversion of compound XIX to XX occurs by hydrogenolysis. Typical hydrogenolysis agents include platinum, palladium on calcium carbonate, palladium on barium sulfate and Raney nickel. For example, the reaction proceeds in the presence of hydroxylic organic solvents (e.g., organic alcohols such as methanol and isopropanol) and at a temperature ranging from about 0° to about 80° C. Room temperature is preferred. The pressure can vary from atmospheric to 500 psi but atmospheric pressure is preferred.

The alcohol of formula XX is converted to an aldehyde of formula XXI by conventional procedures for selectively oxidizing an alcohol without affecting a sulfide. Typical oxidizing agents include chromium trioxide-pyridine complex, pyridinium chlorochromate, and dimethyl sulfoxide. The temperature generally ranges from about −0° to about 30° C.

The aldehyde of formula XXI is then oxidized to d-biotin by reaction with silver oxide. Preferably, the reaction proceeds in an alkali metal hydroxide-water solvent (e.g., aqueous sodium hydroxide and aqueous potassium hydroxide). Although not critical, the reaction generally proceeds from about room temperature to the boiling point of the reaction media. Generally, a temperature of about 60° C. is preferred.

According to another aspect of the present invention, isoxazoline XII is first reduced to isoxazolidine of formula XXII by any hydride reducing agent which is capable of selectively reducing a isoxazoline without attacking a urethane group. Suitable reducing agents include diborane and a dialkyl aluminum hydride (e.g., diisobutylaluminum hydride). This reduction is carried out in an inert solvent such as an aliphatic (e.g., isopropane) or aromatic (e.g., benzene) hydrocarbon or an ether (e.g., diethyl ether). When diborane is utilized, the conversion of compound XII to compound XXII generally proceeds between about −30° and about 30° C. and preferably at about 0° C. When a dialkyl aluminum hydride is utilized, the reaction generally proceeds at about −80° to about −20° C. and preferably at about −60° to about −50° C.

Isoxazolidine XXII is then converted to an amino alcohol of formula XXIII by catalytic hydrogenation in a suitable solvent. Typical catalysts include platinum, palladium on charcoal and Raney nickel. Any organic solvent utilized in conventional catalytic hydrogenation may be employed. Suitable solvents include organic alcohols such as methanol, isopropanol and hexanol as well as acetic acid. Although not critical, the temperature of the noted reaction generally ranges from about 0° to about 50° C. Room temperature is preferred.

Amino alcohol XXIII can then be cyclized to an imidazolone of formula XXIV by treatment with strong base. Suitable bases include alkali metal and alkaline earth metal hydroxide and alkoxides (e.g. sodium hydroxide, barium hydroxide and potassium alkoxide) as well as tertiary amines (pyridine and triethyl amine). Although not necessary, any conventional organic solvent or aqueous mixture thereof may be employed in the reaction. Typical solvents include dioxane and diethyl ether. The temperature of this reaction can range from about 50° to about 150° C. When barium is utilized with a dioxanewater mixture, reflux temperature is preferred.

Imidazolone XXIV can be converted to an olefinic mixture of Z and E geometric isomers of formula XVIII by dehydration. For example, compound XXIV can be reacted in the presence of paratoluene sulfonic acid in an inert aromatic solvent such as toluene to produce geometric isomers of formula XVIII. The temperature of the reaction generally ranges from about 60° C. to about 130° C. When toluene is the solvent, about 100° C. is preferred.

Compound XVIII can then be converted to known compound XIX and ultimately to d-biotin of formula I by the procedures and intermediates described hereinbefore.

In accordance with a particularly preferred process of the instant invention, the mixture of isomers XI and XII need not be separated into individual compounds to form d-biotin. Pursuant to the previously described reaction conditions and procedures, a mixture of compounds XI and XII can be converted to a mixture of compounds XV and XXII, which can be converted to compounds XVI and XXIII, which in turn can be cyclized to a mixture of compounds XVII and XXIV, which can be followed by dehydration to compound XVIII. The latter compound can be converted to known compound XIX which can be converted to d-biotin by the procedures described previously.

Although the above discussions are directed particularly to the conversion of optically active L-cystine of formula II to optically active d-biotin of formula I, the present invention is not to be construed as limited thereto. For example, the process of the present invention may be utilized to convert the racemate of L-cystine to the racemate of d-biotin via racemates of the previously described intermediates.

More particularly, the racemate of L-cystine of formula II can be acylated at the nitrogen to the racemate of urethane III, which can be reduced to the racemate of mercaptan IV, followed by conversion to the racemate of olefinic carboxylic acid V. The latter racemate can then be reduced to a racemate of alcohol VI, which can be converted to the racemate of sulfonate VII, which in turn can be converted to the racemate of compound VIII and subsequently to the racemate of nitro olefin IX. The racemate of compound IX can be dehydrated to the racemates of isomeric isoxazolines XI through XIV. The isomers can then be separated by conventional means. The racemate of compounds XI and/or XII can then be converted to the racemate of isoxazolidine XV and/or XXII, which in turn can then be converted to the racemate of the hydroxy amine XVI and/or XXIII, followed by cyclization to the racemate of imidazolone XVII and/or XXIV. The latter racemate is then dehydrated to the racemate of olefin XVIII, which in turn is catalytically hydrogenated to the racemate of compound XIX. When $R_2$ of racemate XIX is methyl, said racemate can be directly converted to the racemate of biotin I by the process disclosed in U.S. Pat. No. 3,859,167 issued to Ogino et al. When $R_2$ is $—CH_2OR_3$, racemate XIX is converted into the racemate of compound XX which in turn is selectively oxidized to the racemate of aldehyde XXI which then can be converted to the racemate of biotin of formula I. If desired, the racemate of formula I can be converted to d-biotin by conventional resolution techniques and procedures.

If desired, any of the racemates formed by the aforementioned procedure can be converted to its desired optically active enantiomer by conventional resolution procedures. For example, the selected racemate can be reacted with a conventional resolving agent and the reaction products can be separated by known techniques such as crystallization and chromatography. The optically active enantiomer can then be converted to optically active d-biotin by the process previously described.

If desired, any of the Z and E geometric isomer mixtures of formulas V–IX and XVIII can be converted to their corresponding Z and E components via conventional chromatographic techniques. Suitable methods are open column chromatography on silica and high pressure liquid chromatography.

The following examples are illustrative of the instant invention. Unless otherwise indicated, all temperatures are in degrees Centigrade (°C.) and the ether is diethyl ether.

EXAMPLE 1

L-N-(methoxycarbonyl)-cystine

A solution of 13.8 g (0.13 mol) of sodium carbonate, dissolved in 180 ml of water was mixed with 120 ml of a 10% solution of sodium bicarbonate in water, to which 14.4 g (0.06 mol) of L-(—)-cystine were added. The resulting suspension was cooled at 0° C. and treated dropwise with 12.3 g (10.1 ml, 0.13 mol) of methylchloroformate. After addition, the reaction mixture was allowed to come to room temperature and vigorously stirred for 4 hours. It was then cooled again at 0° C. and adjusted to pH 2 with 5 N hydrochloric acid, allowed to come to room temperature, saturated with sodium chloride and extracted with 3×150 ml of ethyl acetate. The combined organic layers were dried and evaporated in vacuo to give 19.16 g (92% crude yield) of L-N-(methoxycarbonyl)-cystine as a thick pale yellow oil.

EXAMPLE 2

L-N-(methoxycarbonyl)-cysteine

A solution of 19.6 g (0.055 mol) of crude L-N-(methoxycarbonyl)-cystine in 200 ml of dry liquid ammonia was treated at −60° C. to −70° C. with metallic sodium added portionwise in small pieces and waiting, after each addition, so that the initially blue solution turned colorless again. Altogether, 4.8 g (0.209) of sodium were used. When the blue color persisted, a few crystals of ammonium chloride were added until the color was discharged and then the ammonia was allowed to evaporate. The residue was treated with 100 ml of a saturated ammonium chloride solution, the pH was adjusted to 2 with 5 N hydrochloric acid, and the solution extracted with 3×150 ml of ethyl acetate. The organic layers were combined, dried and evaporated in vacuo to give 18.0 g (91.4% crude yield) of L-N-(methoxycarbonyl)-cysteine as a thick, pale yellow oil.

EXAMPLE 3

(Z and E)-S-(hexen-1-yl)-N-(methoxycarbonyl)-cysteine

A solution of 10.74 g (0.06 mol) of L-N-(methoxycarbonyl)-cysteine, 7.15 g (10 ml, 0.087 mol) of 1-hexyne and 500 mg of 2,2'-bisazo-(2-methylpropionitrile) in 20 ml of dioxane was heated at 85° C. for 10 hours, cooled at room temperature and diluted with 200 ml of ether and extracted with 3×100 ml of a 2 N solution of sodium hydroxide. The combined alkaline solutions were washed with 3×100 ml of ether and adjusted to pH 2 with 3 N hydrochloric acid (at 0° C.). The resulting mixture was extracted with 3×150 ml of ethyl acetate. The combined organic extracts were washed with 3×50 ml of brine, dried and evaporated to give 14.0 g (89% crude yield) of (Z and E)-S-(hexen-1-yl)-N-(methoxycarbonyl)-cysteine as a pale, yellow oil.

The above mixture of Z and E geometric isomers can be separated into its Z and E components by preparative high pressure liquid chromatography using a Waters Associates Chromatograph Model 244 and an 8'×⅜" BONDAPAK ® column.

The Z component generically can be expressed as:

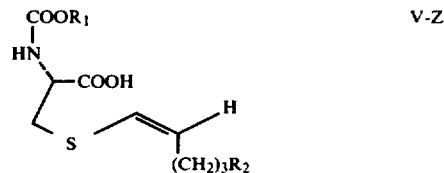

and the E component generically can be described as:

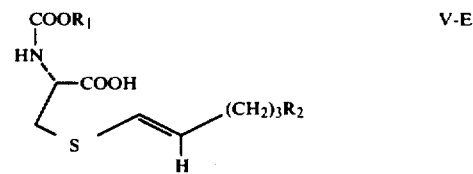

wherein $R_1$ L is lower alkyl or aryl;
$R_2$ is methyl or $—CH_2OR_3$; and,
$R_3$ is lower alkyl, aryl or aryl(lower)alkyl.

EXAMPLE 4

(Z and E)-2R-3-(1-hexen-1-yl-thio)-2-[(methoxycarbonyl)amino]propanol

To a solution of 32.0 g (0.123 mol) of (Z and E)-S-(hexen-1-yl)-N-(methoxycarbonyl)-cysteine in 250 ml of freshly distilled dry tetrahydrofuran cooled at 0° C., 13.6 g (0.134 mol) of triethylamine and 12.8 g (0.135 mol) of methylchloroformate were subsequently added dropwise. After addition, the reaction mixture was stirred for 2½ hours, filtered and slowly added to a suspension of 22.7 g (0.600 mol) of sodium borohydride in 100 ml of water at 0° C. The resulting mixture was allowed to come to room temperature, stirred for 3 hours, cooled again at 0° C. and treated with 65 ml of 5 N hydrochloric acid, which were added dropwise. Finally, the solution was extracted with 3×150 ml of ethyl acetate and the combined organic layers were washed with 3×50 ml of a 2 N potassium bicarbonate solution, followed by 3×50 ml of brine, dried and evaporated in vacuo to give 25.8 g. (87% crude yield) of (Z and E)-2R-3-(1-hexen-1-yl-thio)-2-[(methoxycarbonyl)amino]propanol, as an almost colorless thick oil.

The above mixture Z and E geometric isomers can be separated into its Z and E components by preparative high pressure liquid chromatography using a Waters Associates Chromatograph Model 244 and an 8'×⅜" PORASIL A ® column, eluted with a mixture of n-hexane and ethyl acetate (1:1 parts by volume).

The Z component generically can be expressed as:

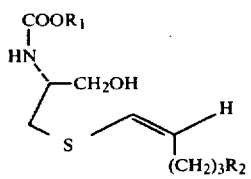

VI-Z and the E component generically can be described as:

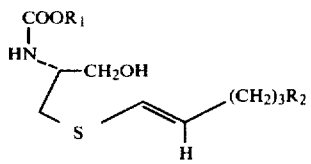

VI-E wherein
$R_1$ is lower alkyl or aryl;
$R_2$ is methyl or $-CH_2OR_3$; and,
$R_3$ is lower alkyl, aryl or aryl(lower)alkyl.

EXAMPLE 5

(Z and E)-2R-3-(1-hexen-1-yl-thio-2-[(methoxycarbonyl)amino]-1-([methylsulfonyl)oxy]propane A solution of 13.1 g (0.050 mol) of (Z and E)-2R-3-(1-hexen-1-yl-thio)-2-[(methoxy carbonyl)amino]propanol in 60 ml of anhydrous pyridine was treated dropwise at 0° C. with 8.6 g (0.075 mol) of methanesulfonylchloride. After addition, the reaction mixture was further stirred at 0° C. for 4 hours. Then, it was diluted with 10 ml of water, stirred for 30 minutes, adjusted to pH 2 with 2 N hydrochloric acid and extracted with 3×100 ml of ethyl acetate. The combined organic phases were washed with water, 2 N potassium bicarbonate solution, brine, dried and evaporated in vacuo to give 16.2 g (99% crude yield) of (Z and E)-2R-3-(1-hexen-1-yl-thio)-2-[(methoxycarbonyl)amino]-1-[(methylsulfonyl)oxy]propane as a thick, pale yellow oil.

The above mixture Z and E geometric isomers can be separated into its Z and E components by preparative high pressure liquid chromatography using a Waters Associates Chromatograph Model 244 and an 8'×⅜" PORASIL A ® column.

The Z component generically can be expressed as:

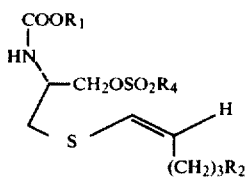

VII-Z and the E component generically can be described as:

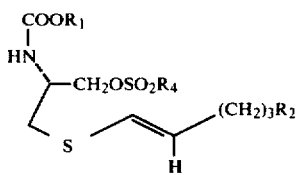

VII-E wherein
$R_1$ and $R_4$ are each lower alkyl or aryl;
$R_2$ is methyl or $-CH_2OR_3$; and
$R_3$ is lower alkyl, aryl or aryl(lower)alkyl.

EXAMPLE 6

(Z and E)-2S-3-(1-hexen-1-yl-thio)-1-iodo-2-[(methoxycarbonyl)amino]propane

A mixture of 16.2 g (0.050 mol) of (Z and E)-2R-3-(1-hexen-1-yl-thio)-2[(methoxy-carbonyl)amino]-1-[(methylsulfonyl)oxy]propane, 22.5 g (0.150 mol) of sodium iodide and 350 ml of acetone was refluxed for 5 hours. After cooling, the solvent was evaporated in vacuo, the residue treated with 100 ml of water and extracted with 3×100 ml of ethyl acetate. The combined organic phases were washed with 2 N sodium thiosulfate solution, water, brine and evaporated in vacuo to give 16.1 g (90.7% crude yield) of (Z and E)-2S-3-(1-hexen-1-yl-thio)-1-iodo-2-[(methoxycarbonyl)amino]propane, as a thick, yellow-brown oil.

The above mixture Z and E geometric isomers can be separated into its Z and E components by preparative high pressure liquid chromatography using a Waters Associates Chromatograph Model 244 and an 8'×⅜" PORASIL A ® column.

The Z component generically can be expressed as:

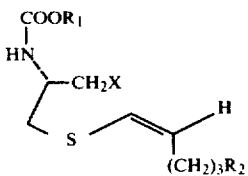

VIII-Z and the E component generically can be described as:

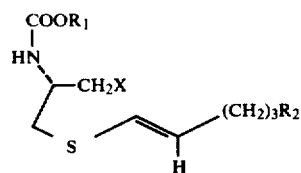

wherein
R₁ is lower alkyl or aryl;
R₂ is methyl or —CH₂OR₃;
R₃ is lower alkyl, aryl or aryl(lower)alkyl; and X is halide.

EXAMPLE 7

(Z and E)-2R-3-(1-hexen-1-yl-thio)-2-[(methoxycarbonyl)amino]-1-nitropropane

A solution of 6.8 g (0.019 mol) of (Z and E)-2S-3-(1-hexen-1-yl-thio)-1-iodo-2-[(methoxycarbonyl)amino]-propane, 2.5 g (0.042 mol) of urea, 2.4 g (0.019 mol) of phloroglucinol and 2.9 g (0.042 mol) of sodium nitrite in 100 ml of dimethylformamide was stirred at room temperature under nitrogen, for 30 hours. The reaction mixture was then treated with 100 ml of water, extracted with 3×100 ml of ether and the combined organic layers were washed subsequently with water, 2 N sodium thiosulfate solution, water, 2 N potassium bicarbonate and brine. Evaporation in vacuo gave 5.39 g of a yellow residue which were purified on a silica gel column (100 g), eluted with an ethyl acetate-hexane mixture (2:3 parts by volume) to give 3.1 g (59% yield) of pure (Z and E)-2R-3-(1-hexen-1-yl-thio)-2-[(methoxycarbonyl)amino]-1-nitropropane as a light yellow powder. Crystallization from methylene chloride-hexane gave 2.9 g. (55%) of crystalline (Z and E)-2R-3-(1-hexen-1-yl-thio)-2-[(methoxycarbonyl)amino]-1-nitropropane, m.p. 75°-76° C.

The above mixture Z and E geometric isomers can be separated into its Z and E components by preparative high pressure liquid chromatography using a Waters Associates Chromatograph Model 244 and an 8'×⅜" PORASIL A ® column.

The Z component generically can be expressed as:

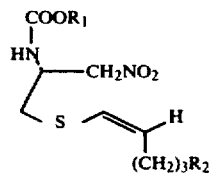

and the E component generically can be described as:

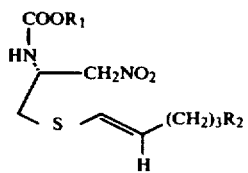

wherein
R₁ is lower alkyl or aryl;
R₂ is methyl or —CH₂OR₃; and,
R₃ is lower alkyl, aryl or aryl(lower)alkyl.

EXAMPLE 8

[3S-(3β,3aβ,6α)], [(3R-(3α,3aβ,6α)], [3S-(3β,3aα,6α)] and
[(3R-(3α,3aα,6α)]-3-butyl-3,3a,5,6,-tetrahydrothieno[3,2-c]isoxazol-6-yl carbamic acid methyl ester A mixture of 1.00 g (0.0036 mol) of (Z and E)-2R-3-(1-hexen-1-yl-thio)-2-[(methoxycarbonyl)amino]-1-nitropropane, and 1.29 g (0.0109 mol) phenylisocyanate in 30 ml of anhydrous benzene to which a few drops of triethylamine were added, was stirred at room temperature, under argon, for 40 hours. The reaction mixture was then treated with 5 ml of water, stirred at room temperature for one hour, diluted with 100 ml of benzene and the organic phase washed subsequently with water and brine, dried and evaporated to give 0.980 g of a light brown residue. This was applied on a 200 g silica gel column, eluted with a 1:2 parts by volume mixture of ethyl acetate-hexane to give 0.859 g (92.4% yield) of a mixture of isoxazolines [3S-(3β,3aβ,6α)], [(3R-(3α,-3aβ,6α)], [3S-(3β,3aα,6α)] and [(3R-(3α,3aα,6α)]-3-butyl-3,3a,5,6-tetrahydrothieno[3,2-c]isoxazol-6-yl carbamic acid methyl ester. The components of the mixture were separated by high pressure chromatography using a Waters Associates Chromatograph Model 244 and an 8'×⅜" PORASIL A ® column, eluted with a mixture of hexane-ethyl acetate (5:1 parts by volume) to give the following isomers: 0.111 mg of pure [(3S-3β,3aβ,6α)]-3-butyl-3,3a,5,6-tetrahydrothieno-3,2-c]isoxazol-6-yl carbamic acid methyl ester. (Crystallization from hexanemethylene chloride afforded white crystals, m.p. 83°-85° C.); 0.149 mg of pure [3R-(3α,-3aβ,6α)]-3-butyl-3,3a,5,6-tetrahydrothieno [3,2-c]isoxazol-6-yl carbamic acid methyl ester. (Crystallization from hexane-methylene chloride gave white crystals, m.p. 110°-113° C.); 0.119 mg of pure [3S-(3β,3aα,6α)]-3-butyl-3,3a,5,6-tetrahydrothieno [3,2-c]-isoxazol-6-yl carbamic acid methyl ester. (Crystallization from methylene chloride hexane afforded white crystals, m.p. 92°-94° C.); and 0.122 mg of pure [3R-(3α,3aα,6α)]-3-butyl-3,3a,5,6-tetrahydrothieno [3,2-c]isoxazol-6-yl carbamic acid methyl ester. (Crystallization from methylene chloride-hexane gave white crystals, m.p. 102°-104° C.)

EXAMPLE 9

[3S-(3β,6α)cis]-3-butylhexahydrothieno[3,2-c]-isoxazol-6-yl carbamic acid methyl ester and
[3R-(3α,6α)cis]-3-butylhexahydrothieno[3,2-c]-isoxazol-6-yl-carbamic acid methyl ester To a solution of 1.4 g (5.4 mmol) of the isomeric isoxazolines [3S-(3β,3aβ,6α)] and [3R-(3α,3aβ,6α)]-3-butyl-3,3a,5,6-tetrahydrothieno[3,2-c]isoxazol-6-yl carbamic acid methyl ester (approx. 1:1 mixture) in 60 ml of anhydrous toluene, kept under argon at −78° C., 18 ml (27.0 mmol) of a 1.5 molar diisobutylaluminum hydride solution in toluene were added dropwise. After addition, the reaction mixture was stirred at −78° C. for one additional hour. After this time, 5 ml of methanol were added dropwise, the solution was allowed to come to room temperature and was mixed with 100 ml of a 2 N aqueous Rochelle salt solution. The organic layer was separated and the aqueous phase further extracted with 3×50 ml of ethyl acetate. The combined organic phases were washed with brine, dried and evaporated in vacuo to give 1.4 g of a crude mixture of [3S-(3β,6α)- cis]-3-butylhexahydrothieno[3,2-c]-isoxazol-6-yl carbamic acid methyl ester and [3R-(3α,6α)-cis]-3-butyl-hexahydrothieno[3,2-c]-isoxazol-6-yl-carbamic acid methyl ester. The components of this mixture was separated on a 250 g silica gel column, using ethyl acetate-hexane (1:1 parts by volume) as eluent to give 0.380 g of pure [3S-(3β,6α)cis]-3-butylhexahydrothieno[3,2-c]-isoxazol-6-yl carbamic acid methyl ester and 0.280 g. of pure [3R,(3α,6α)cis]-3-butylhexahydrothieno[3,2-c]-isoxazol-6-yl-carbamic acid methyl ester. Crystallization of [3S-(3β,6α)cis]-3-butylhexahydrothieno[3,2-c]-isoxazol-6-yl-carbamic acid methyl ester from hexane-methylene chloride gave white crystals, m.p. 143°-144° C. Crystallization of [3R-(3α,6α)cis]-3-butylhexahydrothieno[3,2-c]-isoxazol-6-yl-carbamic acid methyl ester from methylene chloride-hexane afforded white crystals, m.p. 147°-149° C.

EXAMPLE 10

[2R-(2R*)-(2α,3α,4α)]-3-amino-α-butyl-tetrahydro-4-[(methoxycarbonyl)amino]thiophene 2-methanol A mixture of 0.175 g (0.672 mmol) of [3S-(3β,6α)cis]-3-butylhexahydrothieno[3,2-c]isoxazol-6-yl carbamic acid methyl ester and 0.050 g of 10% palladium on charcoal in 15 ml of a 1:1 parts by volume mixture of acetic acid and water was hydrogenated at room temperature and under atmospheric pressure for 24 hours. The resulting solution was then neutralized by careful addition of 1 N potassium bicarbonate solution and, after addition of 50 ml of ethyl acetate, filtered through Celite ® (diatomaceous silica product manufactured by Johns-Manville Corp.) and washed with 5×50 ml of ethyl acetate. The separated and combined organic layers were washed with 3×20 ml of brine, dried and evaporated in vacuo to give 0.164 g (93% yield) of crude [2R-(2R*)-(2α,3α,4α)]-3-amino-α-butyl-tetrahydro-4-[(methoxycarbonyl)amino]thiophene-2-methanol. This was further purified by column chromatography on 30 g of silica gel, using ethyl acetate-methanol (95:5 parts by volume) as eluent to give 0.111 g (63% yield) of pure [2R-(2R*)-(2α,3α,4α)]-3-amino-α-butyl-tetrahydro-4-[(methoxycarbonyl)amino]thiophene-2-methanol. Crystallization from methylene chloride-methanol gave white crystals, m.p. 134°-135° C.

EXAMPLE 11

[2R-(2S*)-(2α,3α,4α)-3-amino-α-butyl-tetrahydro-4-(methoxycarbonyl)amino]thiophene-2-methanol A mixture of 0.120 g (0.461 mmol) of [3R-(3α,6α)cis]-3-butylhexahydrothieno [3.2-c]isoxazol-6-yl-carbamic acid methyl ester and 0.050 g of 10% palladium on charcoal in 15 ml of a 1:1 parts by volume mixture of acetic acid and water was hydrogenated at room temperature and under atmospheric pressure for 24 hours. The reaction mixture was then neutralized by careful addition of 1 N potassium bicarbonate solution and after addition of 50 ml of ethyl acetate, filtered through Celite ® (diatomaceous silica product manufactured by Johns-Manville Corp.) and washed with 5×10 ml of ethyl acetate. The separated and combined organic layers were washed with 3×20 ml of brine, dried and evaporated in vacuo to give 0.113 g (93% yield) of crude [2R-(2S*)-(2α,3α,4α)-3-amino-α-butyl-tetrahydro-4-(methoxycarbonyl)amino]thiophene-2-methanol. Purification by column chromatography gave 0.086 g. (71%) of pure [2R-(2S*)-(2α,3α,4α)-3-amino-α-butyl-tetrahydro-4-(methoxycarbonyl)amino]thiophene-2-methanol. Crystallization from hexane-methylene chloride gave white crystals, m.p. 104°-105° C.

EXAMPLE 12

[3aS,4R,(4R*),3aβ,6aβ]-4-(1-hydroxypentyl)-1H-hexahydrothieno[3,4-d]imidazol-2-one A mixture of 0.014 g (0.053 mmol) of [2R-(2R*)-(2α,3α,4α)]-3-amino-α-butyl-tetrahydro-4-[(methoxycarbonyl)amino]thiophene-2-methanol, 0.2 g of barium hydroxide, 1 ml of dioxane and 2 ml of water was refluxed under argon for 1 hour. The mixture was then acidified with 1 N hydrochloric acid and extracted with 4×20 ml of ethyl acetate. The combined organic layers were washed with 2 N potassium bicarbonate solution and brine, dried and evaporated in vacuo to give 0.0115 g (93%) of [3aS,4R,(4R*),3aβ,6aβ]-4-(1-hydroxypentyl)-1H-hexahydrothieno[3,4-d]imidazol-2-one. Crystallization from methylene chloride-hexane gave white crystals, m.p. 222°-224° C.

EXAMPLE 13

[3aS,4R-(4S*),3aβ,6aβ]-4-[1-hydroxypentyl]-1H-hexahydrothieno[3,4-d]imidazol-2-one A mixture of 0.030 g (0.114 mmol) of [2R-(2S*)-(2α,3α,4α)]-3-amino-α-butyl-tetrahydro-4-[(methoxycarbonyl)amino]thiophene-2-methanol and 0.2 g of barium hydroxide, 1.5 ml of dioxane and 2 ml of water was refluxed under argon for 1 hour. The mixture was then acidified with 1 N hydroxhloric acid and extracted with 4×20 ml of ethyl acetate. The combined organic layers were washed with 2 N potassium bicarbonate solution and brine, dried and evaporated in vacuo to give 0.0215 g (82% yield) of [3aS,4R-(4S*),3aβ,6aβ]-4-[1-hydroxyphentyl]-1H-hexahydrothieno[3,4-d]imidazol-2-one. Crystallization from methyl chloride-hexane gave white crystals, m.p. 196°-198° C.

EXAMPLE 14

(E and Z)-[3aS,3aβ,4α,6aβ]-4-(1-penten-1-yl)-1H-hexahydrothieno[3,4-d]imidazol-2-one A solution of 0.08 g (0.35 mmol) of [3aS,4R-(4R*)-3aβ,6aβ]-4-[1-hydroxypentyl]-1H-hexahydrothieno[3,4-d]imidazol-2-one and 0.020 g of p-toluenesulphoric acid monohydrate in 2 ml of dry toluene was refluxed for 1 hour under argon. After cooling, 5 ml of a 2 N sodium bicarbonate solution were added thereto and the resulting mixture was extracted with 3×20 ml of ethyl acetate. The combined organic phases were washed with brine and dried to give, after evaporation of the solvent in vacuo, 0.072 g (98% yield) of (E and Z)-[3aS,3aβ,4α,6aβ]-4-(1-penten-1-yl)-1H-hexahydrothieno[3,4-d]imidazol-2-one. NMR analysis showed in the presence of a 5:2 ratio of E and Z geometrical isomers.

The above mixture Z and E geometric isomers can be separated into its Z and E components by preparative high pressure liquid chromatography using a Waters Associates Chromatograph Model 244 and an 8'×⅜" PORASIL A ® column.

The Z component generically can be expressed as:

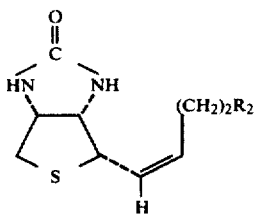

and the E component generically can be described as:

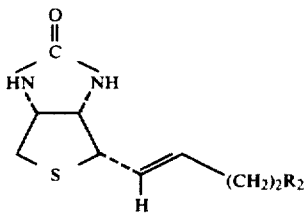

wherein

R₁ is lower alkyl or aryl;

R₂ is methyl or —CH₂OR₃; and,

R₃ is lower alkyl, aryl or aryl (lower) alkyl.

EXAMPLE 15

(E and Z)-[3aS,3aβ,4α,6aβ]-4-(1-hexen-1-yl)-1H-hexahydro-thieno[3,4-d]imidazol-2-one A solution of 0.10 g (0.43 mmol) of [3aS,4R-(4S*)-3aβ,6aβ]-4-[1-hydroxypentyl]-1H-hexahydro-thieno[3,4-d]imidazol-2-one and 0.020 g of p-toluenesulfonic acid monohydrate in 2 ml of dry toluene was refluxed under argon for 1 hour. After cooling, 5 ml of a 2 N sodium bicarbonate solution were added thereto and the resulting mixture was extracted with 3×20 ml of ethyl acetate. The combined organic phases were washed with brine and dried to give after evaporation of the solvent in vacuo, 0.09 g (92% yield) of (E and Z)-[3aS,3aβ,4α,6aβ]-4-(1-hexen-1-yl)-1H-hexahydro-thieno[3,4-d]imidazol-2-one.

The above mixture Z and E geometric isomers can be separated into its Z and E components by preparative high pressure liquid chromatography using a Waters Associates Chromatograph Model 244 and an 8' × ⅜" PORASIL A ® column.

The Z component generically can be expressed as:

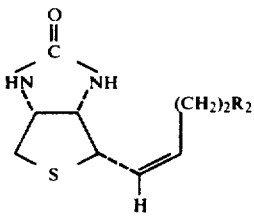

and the E component generically can be described as:

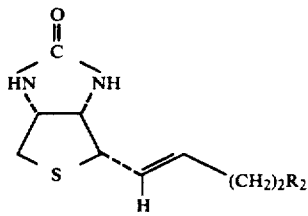

wherein

R₁ is lower alkyl or aryl;

R₂ is methyl or —CH₂OR₃; and,

R₃ is lower alkyl, aryl or aryl(lower)alkyl.

EXAMPLE 16

[3aS,3aβ,4α,6aβ]-hexahydro-4-pentyl-1H-thieno[3,4-d]imidazol-2-one

A mixture of 0.026 g (0.122 mmol) of (E and Z)-[3aS,-3aβ,4α,6aβ]-4-(1-hexen-1-yl)-1H-hexahydrothieno[3,4-d]-imidazol-2-one, 8 ml of a 1:1 parts by volume mixture of acetic acid and water and 50 mg of 10% palladium on charcoal was hydrogenated at room temperature and under atmospheric pressure overnight. It was then neutralized by careful addition of 2 N potassium bicarbonate solution and, after addition of 50 ml of ethyl acetate, filtered through Celite ® (diatomaceous silica product manufactured by Johns-Manville Corp.) and washed with 3×20 ml of ethyl acetate. The separated and combined organic layers were washed with brine, dried and evaporated in vacuo to give 0.024 g (92% yield) of [3aS,3aβ,4α,6aβ]-hexahydro-4-pentyl-1H-thieno[3,4-d]-imidazol-2-one. Crystallization from ethanol-water gave white crystals, m.p. 182°–183° C.

We claim:

1. A compound of the formula:

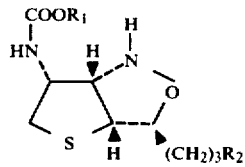

wherein

R₁ is lower alkyl, phenyl or naphthyl;

R₂ is —CH₃ or —CH₂OR₃; and

R₃ is lower alkyl, phenyl, naphthyl, benzyl or α-lower alkyl benzyl; said phenyl and naphthyl each are unsubstituted or substituted with a halogen, lower alkylenedioxy having 2 to 5 carbon atoms, lower alkyl or lower alkoxy, with the lower alkyl and lower alkoxy moieties each having 1 to 7 carbon atoms, or the racemate thereof.

2. The compound of claim 1 wherein the compounds is:

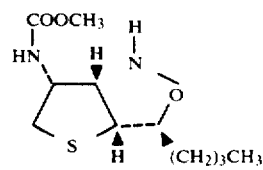

3. A compound of the formula:

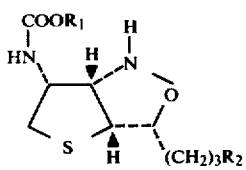

wherein
R₁ is lower alkyl, phenyl or naphthyl;
R₂ is —CH₃ or —CH₂OR₃; and
R₃ is lower alkyl, phenyl, nphthyl, benzyl or α-lower alkyl benzyl; said phenyl and naphthyl each are unsubstituted or substituted with a halogen, lower alkylenedioxy having 2 to 5 carbon atoms, lower alkyl or lower alkoxy, with the lower alkyl and lower alkoxy moieties each having 1 to 7 carbon atoms,
or the racemate thereof.

4. The compound of claim 3 wherein the compound is:

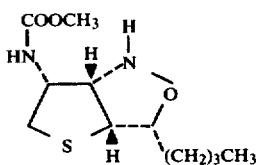

5. A compound of the formula:

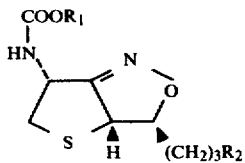

wherein
R₁ is lower alkyl, phenyl or naphthyl;
R₂ is —CH₃ or —CH₂OR₃; and
R₃ is lower alkyl, phenyl, naphthyl, benzyl or α-lower alkyl benzyl; said phenyl and naphthyl each are unsubstituted or substituted with a halogen, lower alkylenedioxy having 2 to 5 carbon atoms, lower alkyl or lower alkoxy, with the lower alkyl and lower alkoxy moieties each having 1 to 7 carbon atoms,
or the racemate thereof.

6. The compound of claim 5 wherein the compound is:

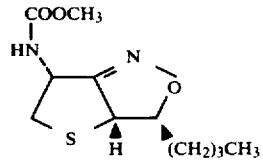

7. A compound of the formula:

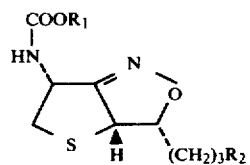

wherein
R₁ is lower alkyl, phenyl or naphthyl;
R₂ is —CH₃ or —CH₂OR₃; and
R₃ is lower alkyl, phenyl, naphthyl, benzyl or α-lower alkyl benzyl; said phenyl and naphthyl each are unsubstituted or substituted with a halogen, lower alkylenedioxy having 2 to 5 carbon atoms, lower alkyl or lower alkoxy, with the lower alkyl and lower alkoxy moieties each having 1 to 7 carbon atoms,
or the racemate thereof.

8. The compound of claim 7 wherein the compound is:

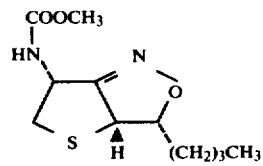

* * * * *